US008980840B2

(12) United States Patent
Truitt, III et al.

(10) Patent No.: US 8,980,840 B2
(45) Date of Patent: Mar. 17, 2015

(54) THERAPEUTIC MODULATION OF VAGINAL EPITHELIUM BOUNDARY LUBRICATION

(75) Inventors: Edward R. Truitt, III, San Diego, CA (US); Benjamin Sullivan, San Diego, CA (US); David Sullivan, Boston, MA (US)

(73) Assignees: Schepens Eye Research Institute, Boston, MA (US); Lubris LLC, Framingham, MA (US)

( * ) Notice: Subject to any disclaimer, the term of this patent is extended or adjusted under 35 U.S.C. 154(b) by 457 days.

(21) Appl. No.: 13/144,203

(22) PCT Filed: Jan. 13, 2010

(86) PCT No.: PCT/US2010/020929
§ 371 (c)(1),
(2), (4) Date: Nov. 8, 2011

(87) PCT Pub. No.: WO2010/083239
PCT Pub. Date: Jul. 22, 2010

(65) Prior Publication Data
US 2012/0052077 A1 Mar. 1, 2012

Related U.S. Application Data

(60) Provisional application No. 61/260,402, filed on Nov. 12, 2009, provisional application No. 61/144,344, filed on Jan. 13, 2009.

(51) Int. Cl.
| | | |
|---|---|---|
| A61K 38/14 | (2006.01) | |
| A61K 9/00 | (2006.01) | |
| A61K 9/02 | (2006.01) | |
| A61K 9/06 | (2006.01) | |
| A61K 31/70 | (2006.01) | |
| A61K 31/715 | (2006.01) | |
| A61K 38/13 | (2006.01) | |
| A61K 38/24 | (2006.01) | |
| A61K 45/06 | (2006.01) | |
| A61K 38/17 | (2006.01) | |
| A61K 38/20 | (2006.01) | |

(52) U.S. Cl.
CPC ............. *A61K 9/0034* (2013.01); *A61K 9/02* (2013.01); *A61K 9/06* (2013.01); *A61K 31/70* (2013.01); *A61K 31/715* (2013.01); *A61K 38/13* (2013.01); *A61K 38/24* (2013.01); *A61K 45/06* (2013.01); *A61K 38/1709* (2013.01); *A61K 38/1793* (2013.01); *A61K 38/20* (2013.01)
USPC ........................................................ 514/20.9

(58) Field of Classification Search
None
See application file for complete search history.

(56) References Cited

U.S. PATENT DOCUMENTS

| | | | |
|---|---|---|---|
| 5,326,558 A | 7/1994 | Turner et al. | |
| 6,433,142 B1 | 8/2002 | Turner et al. | |
| 6,743,774 B1 | 6/2004 | Jay et al. | |
| 6,960,562 B2 | 11/2005 | Jay et al. | |
| 7,030,223 B2 | 4/2006 | Turner et al. | |
| 7,361,738 B2 | 4/2008 | Turner et al. | |
| 7,405,303 B2* | 7/2008 | Hoekstra et al. | 546/173 |
| 7,642,236 B2 | 1/2010 | Flannery et al. | |
| 2002/0028227 A1 | 3/2002 | Yu et al. | |
| 2003/0059489 A1 | 3/2003 | Letourneau et al. | |
| 2007/0004694 A1 | 1/2007 | Woolfson et al. | |
| 2007/0275032 A1 | 11/2007 | Wimmer et al. | |
| 2008/0090772 A1 | 4/2008 | Yu et al. | |
| 2008/0286211 A1* | 11/2008 | Barker | 424/45 |
| 2010/0284937 A1* | 11/2010 | Zhao et al. | 424/43 |

OTHER PUBLICATIONS

Zappone et al., "Molecular Aspects of Boundary Lubrication by Human Lubricin: Effects of Disulfide Bonds and Enzymatic Digestion", Langmuir, 2008, pp. 1495-1508.*
Thapa et al., "Herpes Simplex Virus Type 2-Induced Mortality following Genital Infection Is Blocked by Anti-Tumor Necrosis Factor Alpha Antibody in CXCL10-Deficient Mice", Journal of Virology, 2008, pp. 10295-10301.*
Berman et al., Female Sexual Dysfunction: New Perspective on Anatomy, Physiology, Evaluation, and Treatment, EAU Update Series 1, 2003, pp. 166-177.*
International Search Report dated Sep. 17, 2010 for PCT/US2010/020929.

* cited by examiner

*Primary Examiner* — Karlheinz R Skowronek
*Assistant Examiner* — Lianko Garyu
(74) *Attorney, Agent, or Firm* — Thomas E. Jurgensen; Optima Law Group, APC

(57) ABSTRACT

The present invention relates to the management of vaginal health. In particular, the present invention relates to pharmaceutical compositions, and methods of use thereof, for treating diseases associated with compromised boundary lubrication at the vaginal epithelium.

15 Claims, 3 Drawing Sheets

Lane 1 (far left): 100 base pair ladder.

Lane 2: No template control.

Lane 3. Human bladder mRNA.

Lane 4. Human prostate mRNA.

Lane 5. Human cervix mRNA.

Lane 6 (far right). Human uterus mRNA.

|  | Lane # |  |
|---|---|---|
|  | 1- DNA Markers | 10- No Template Control |  |
|  | 2- No Template Control | 11- Seminal Vesicle 1 |  |
|  | 3- Uterus 1 | 12- Seminal Vesicle 2 |  |
|  | 4- Uterus 2 | 13- Seminal Vesicle 3 |  |
|  | 5-Uterus 3 | 14- Male 1 Bladder |  |
|  | 6- Vagina 1 | 15- Male 2 Bladder |  |
|  | 7- Vagina 2 | 16- Male 3 Bladder |  |
|  | 8- Vagina 3 | 17- Female 1 Bladder |  |
|  | 9- DNA Markers | 18- Female 2 Bladder |  |

FIGURE 3

SEQ ID NO:1

MAWKTLPIYLLLLLSVFVIQQVSSQDLSSCAGRCGEGYSRDATCNCDYNCQHYMECCP
DFKRVCTAELSCKGRCFESFERGRECDCDAQCKKYDKCCPDYESFCAEVHNPTSPPSSK
KAPPPSGASQTIKSTTKRSPKPPNKKKTKKVIESEEITEEHSVSENQESSSSSSSSSSSTIRK
IKSSKNSAANRELQKKLKVKDNKKNRTKKKPTPKPPVVDEAGSGLDNGDFKVTTPDTS
TTQHNKVSTSPKITTAKPINPRPSLPPNSDTSKETSLTVNKETTVETKETTTTNKQTSTDG
KEKTTSAKETQSIEKTSAKDLAPTSKVLAKPTPKAETTTKGPALTTPKEPTPTTPKEPAST
TPKEPTPTTIKSAPTTPKEPAPTTTKSAPTTPKEPAPTTTKEPAPTTPKEPAPTTTKEPAPTT
TKSAPTTPKEPAPTTPKKPAPTTPKEPAPTTPKEPTPTTPKEPAPTTKEPAPTTPKEPAPTA
PKKPAPTTPKEPAPTTPKEPAPTTTKEPSPTTPKEPAPTTTKSAPTTTKEPAPTTTKSAPTT
PKEPSPTTTKEPAPTTPKEPAPTTPKKPAPTTPKEPAPTTPKEPAPTTTKKPAPTTPKEPAP
TTPKETAPTTPKKLTPTTPEKLAPTTPEKPAPTTPEELAPTTPEEPTPTTPEEPAPTTPKAA
APNTPKEPAPTTPKEPAPTTPKEPAPTTPKETAPTTPKGTAPTTLKEPAPTTPKKPAPKEL
APTTTKEPTSTTCDKPAPTTPKGTAPTTPKEPAPTTPKEPAPTTPKGTAPTTLKEPAPTTPK
KPAPKELAPTTTKGPTSTTSDKPAPTTPKETAPTTPKEPAPTTPKKPAPTTPETPPPTTSEV
STPTTTKEPTTIHKSPDESTPELSAEPTPKALENSPKEPGVPTTKTPAATKPEMTTTAKDK
TTERDLRTTPETTTAAPKMTKETATTTEKTTESKITATTTQVTSTTTQDTTPFKITTLKTT
TLAPKVTTTKKTITTTEIMNKPEETAKPKDRATNSKATTPKPQKPTKAPKKPTSTKKPKT
MPRVRKPKTTPTPRKMTSTMPELNPTSRIAEAMLQTTTRPNQTPNSKLVEVNPKSEDAG
GAEGETPHMLLRPHVFMPEVTPDMDYLPRVPNQGIIINPMLSDETNICNGKPVDGLTTLR
NGTLVAFRGHYFWMLSPFSPPSPARRITEVWGIPSPIDTVFTRCNCEGKTFFFKDSQYWR
FTNDIKDAGYPKPIFKGFGGLTGQIVAALSTAKYKNWPESVYFFKRGGSIQQYIYKQEPV
QKCPGRRPALNYPVYGETTQVRRRRFERAIGPSQTHTIRIQYSPARLAYQDKGVLHNEV
KVSILWRGLPNVVTSAISLPNIRKPDGYDYYAFSKDQYYNIDVPSRTARAITTRSGQTLS
KVWYNCP

SEQ ID NO:2: GATGCAGGGTACCCCAAA (human, sense)
SEQ ID NO:3: CAGACTTTGGATAAGGTCTGCC (human, antisense)

THERAPEUTIC MODULATION OF VAGINAL EPITHELIUM BOUNDARY LUBRICATION

CROSS-REFERENCE

This application is a 35 U.S.C. §371 U.S. National Stage application of International Patent Application No. PCT/US2010/20929, filed Jan. 13, 2010, and claims the benefit of U.S. Provisional Application No. 61/144,344, filed Jan. 13, 2009, and U.S. Provisional Application No. 61/260,402, filed Nov. 12, 2009, which applications are incorporated herein by reference in their entireties.

FIELD OF THE INVENTION

The present invention relates to the management of vaginal health. In particular, the present invention relates to pharmaceutical compositions, and methods of use thereof, including for treatment of diseases associated with compromised boundary lubrication at the vaginal surface (e.g., epithelium).

BACKGROUND

The proteoglycan 4 (prg4) gene codes for highly glycosylated proteins termed megakaryocyte stimulating factor (MSF), lubricin, and superficial zone protein (SZP). Lubricin was first isolated from synovial fluid and demonstrated lubricating ability in vitro similar to synovial fluid at a cartilage-glass interface. Lubricin was later identified as a product of synovial fibroblasts. O-linked β(1-3)Gal-GalNAc oligosaccharides within a large mucin like domain of 940 amino acids, encoded for by exon 6, have also been described. SZP was first localized at the surface of explant cartilage from the superficial zone and isolated from conditioned medium. These molecules (as well as O-linked proteoglycans thereof) are collectively referred to herein as PRG4. PRG4 has been shown to be present at the surface of synovium, tendon, and meniscus, but there has been no description of using PRG4 as a lubricant in the vagina.

SUMMARY OF THE INVENTION

The present invention provides, in various embodiments, pharmaceutical compositions, and methods of use thereof, for managing vaginal lubrication, including the therapeutic replenishment and enrichment of boundary lubricant molecules at the vaginal epithelium. Described in certain embodiments of the present invention is the observation that PRG4 mRNA is expressed in mouse vaginal and cervical epithelial cells, indicating that PRG4 protein is secreted by these tissues onto the vaginal epithelium. FIG. 1 illustrates human PRG4 mRNA expression, as demonstrated by agarose electrophoresis following amplification in vaginal and cervical tissue. mRNA was verified through sequencing. FIG. 2 illustrates PRG4 mRNA expression in various mouse epithelial cells. Amplified samples were screened for the presence of PRG4 products by using agarose gel electrophoresis. Vertical lanes 6-8 contain amplified, verified PRG4 mRNA from vaginal tissues of 3 different mice.

Described in certain instances of the present invention is the observation that the role PRG4 protein serves on the vaginal epithelium is to protect the vaginal cavity against significant shear forces generated during intercourse, birthing, and other undesirable conditions. Further described in certain instances of the present invention is the observation that the molecular mechanisms of boundary lubrication found in cartilage, including the ability of secreted components to mediate shear stress in the presence of dynamic loading, are likely useful when utilized for lubricating the vaginal epithelium.

In certain embodiments, the present invention provides a pharmaceutical composition suitable for topical application to the vaginal surface of a patient of a preparation containing a therapeutic amount of a therapeutically effective concentration of a PRG4 protein (including e.g., a PRG4 O-linked proteoglycan) suspended in a gel, aqueous osmotically balanced salt solution, multiphasic emulsification, or encapsulated within slow-release devices.

In certain embodiments, the pharmaceutical composition of the present invention further comprises a therapeutically effective concentration of one or more additional therapeutic agents, e.g., an agent that provides a vaginal benefit and/or has efficacy when administered vaginally. In certain embodiments, an additional agent, includes, but is not limited to, an androgen or androgen analogue, where the androgen or androgen analogue is a 17α-methyl-17β-hydroxy-2-oxa-5α-androstan-3-one derivative, estrogen or estrogen analogue, a nitrogen-substituted androgen, a nitrogen-substituted estrogen, a testosterone derivative, an estrogen derivative, a 4,5α-dihydrotestosterone derivative, a 19-nortestosterone derivative, a 17β-hydroxy-5α-androstane derivative containing a ring A unsaturation, or is from a structural subclass of androgens comprising androgenic compounds with unusual structural features. Or the preparation contains selective androgen receptor modulator (SARM) compounds, which are aryl-propionamide (e.g. S-3-(4-acetylamino-phenoxy)-2-hydroxy-2-methyl-N-(4-nitro-3-trifluoromethyl-phenyl)-propionamide [S-4], or S-3-(4-fluorophenoxy)-2-hydroxy-2-methyl-N-(4-nitro-3-trifluoromethyl-phenyl)-propionamide [S-1]), bicyclic hydantoin, quinoline, and tetrahydroquinoline analogues that have in-vivo androgenic and anabolic activity of a non-steroidal ligand for the androgen receptor, selective estrogen receptor modulator (SERM) compounds, which are non-steroidal ligands of the estrogen receptor that are capable of inducing a number of conformational changes in the receptor and thereby eliciting a variety of distinct biological profiles, estrogen antagonists (steroidal, non-steroidal) irregardless of receptor affinity, aromatase inhibitors, antiproteases, proinflammatory cytokine antagonists (e.g. anti-TNFα antibody, soluble TNFα receptor, IL-1 receptor antagonist), cytokine release inhibitors, NF-κB inhibitors, antiinflammatory cytokines (e.g. TGF-β), other anti-inflammatory agents (e.g. cyclosporine A, omega 3 and 6 fatty acids), or proteasome inhibitors.

In certain embodiments, the pharmaceutical composition of the present invention further comprises a therapeutically effective concentration of one or more additional therapeutic agents, including but not limited to, sodium hyaluronate, hyaluronic acid, and phospholipid. Exemplary phospholipid includes, but is not limited to, L-α-dipalmitoylphosphatidylcholine, phosphatidylcholine, phosphatidylethanolamine and sphingomyelin.

In certain embodiments the pharmaceutical composition of the present invention further comprises a therapeutically effective concentration of compounds that promote epithelial growth and proper morphology, including estrogen, progesterone, follicle stimulating hormone, leutinizing hormone, or other molecules to promote epithelial growth.

The present invention provides a method for treating a deficiency in vaginal lubrication or symptoms associated therewith. Such method comprises topically administering to the vaginal surface of a patient in need the pharmaceutical composition of the present invention. Symptoms of vaginal lubrication deficiency include, vaginal dryness, vaginal itch or a burning sensation, painful sexual intercourse, and light vaginal bleeding after intercourse.

In certain embodiments, the present invention further provides a method for addressing and treating the conditions associated with unfavorable or deficient vaginal lubrication. Exemplary conditions include, but are not limited to vaginal atrophy, dyspareunia, Sjögren's syndrome, menopause, androgen deficiency, estrogen deficiency, estrogen replacement therapy, allergy, chronic inflammation, menopause, premature menopause, chemotherapy, breastfeeding, surgical removal of the ovaries before menopause, genital lichen sclerosis, vulvodynia, bacterial vaginosis, herpes, candida, psoriasis, contact dermatitis, condylomata, side effects of medications and aging.

The present invention provides a method for increasing boundary lubrication during intercourse comprising attaching boundary lubricant molecules to the surface of prophylactics and/or within implantable eluting devices, using supplementation to replenish boundary lubrication over the course of wear; for instance, the supplementation of PRG4 and/or hyaluronic acid in the presence of a PRG4-coated prophylactic surface.

In some embodiments, the therapeutic composition comprises phosphate buffered saline, hyaluronic acid, sodium hyaluronate, or combinations therein.

Other features and advantages of the invention will be apparent from the following description of the preferred embodiments thereof and from the claims.

INCORPORATION BY REFERENCE

All publications and patent applications mentioned in this specification are herein incorporated by reference for the purpose cited.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 illustrates an amino acid sequence of PRG4 as well as nucleic acid primer sequences for PCR amplification of the PRG4 mRNA.

DETAILED DESCRIPTION OF THE INVENTION

Figure 1:
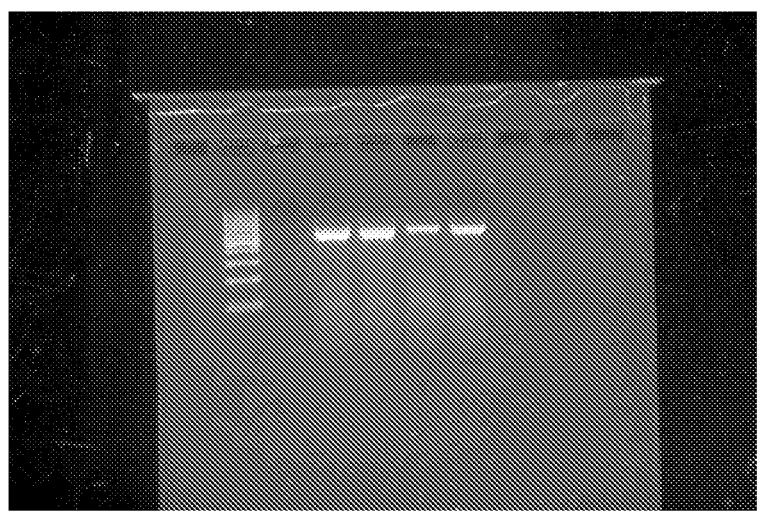
FIG. 1 illustrates human PRG4 mRNA expression, as demonstrated by agarose electrophoresis following amplification in vaginal and cervical tissue. mRNA was verified through sequencing.
Figure 2:
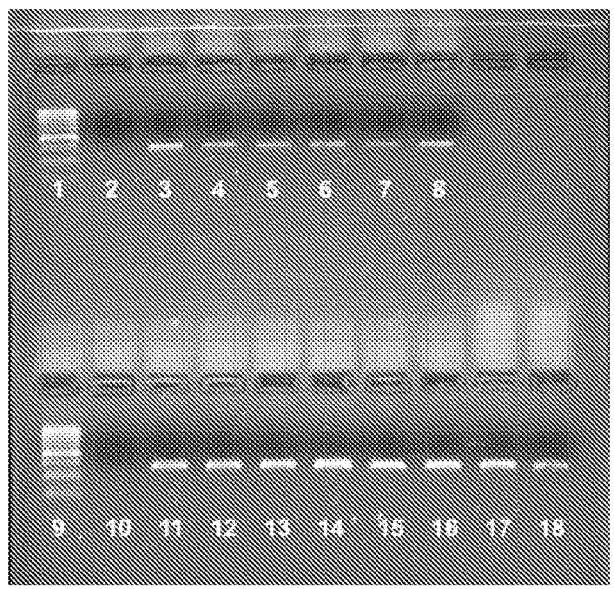
FIG. 2 illustrates PRG4 mRNA expression in various mouse epithelial cells. Amplified samples were screened for the presence of PRG4 products by using agarose gel electrophoresis. Vertical lanes 6-8 contain amplified, verified PRG4 mRNA from vaginal tissues of 3 different mice.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The functional importance of prg4 was shown by mutations that cause the camptodactyly-arthropathy-coxa vara-pericarditis (CACP) disease syndrome in humans. CACP is manifest by camptodactyly, noninflammatory arthropathy, and hypertrophic synovitis, with coxa vara deformity, pericarditis, and pleural effusion. Also, in PRG4-null mice, cartilage deterioration and subsequent joint failure were observed. Therefore, PRG4 expression is a necessary component of healthy synovial joints.

PRG4 is a member of the mucin family, which are generally abundant on epithelial linings and provide many functions, including lubrication and protection from invading microorganisms. The functional properties of mucins are generally determined by specialized glycosylation patterns and their ability to form multimers through intermolecular disulfide bonds, both of which are altered in chronic diseases (e.g. cystic fibrosis, asthma). Biochemical characterization of PRG4 isolated from synovial fluid showed molecular heterogeneity in O-glycosylation, which appears to mediate lubricating properties. Preliminary data on PRG4 from bovine synovial fluid has revealed the presence of disulfide-bonded dimers, in addition to the monomeric forms, predicted from the conserved cysteine-rich domains at both N- and C-terminals, along with an unpaired cysteine at the C-terminal.

Physicochemical modes of lubrication have been classified as fluid film or boundary. The operative lubrication modes depend on the normal and tangential forces on the articulating tissues, on the relative rate of tangential motion between these surfaces, and on the time history of both loading and motion. The friction coefficient, $\mu$, provides a quantitative measure, and is defined as the ratio of tangential friction force to the normal force. One type of fluid-mediated lubrication mode is hydrostatic. At the onset of loading and typically for a prolonged duration, interstitial fluid becomes pressurized, due to the biphasic nature of tissue; fluid may also be forced into the asperities between articular surfaces through a weeping mechanism. Pressurized interstitial fluid and trapped lubricant pools may therefore contribute significantly to the bearing of normal load with little resistance to shear force, facilitating a very low $\mu$. Also, at the onset of loading and/or motion, squeeze film, hydrodynamic, and elastohydrodynamic types of fluid film lubrication occur, with pressurization, motion, and deformation acting to drive viscous lubricant from and/or through the gap between two surfaces in relative motion.

In some instances, the relevant extent to which fluid pressure/film versus boundary lubrication occurs depends on a number of factors. When lubricant film can flow between the conforming sliding surfaces, which can deform elastically, elastohydrodynamic lubrication occurs. Pressure, surface roughness, and relative sliding velocity determine when full fluid lubrication begins to break down and the lubrication enters new regimes. As velocity decreases further, lubricant films adherent to the articulating surfaces begin to contribute and a mixed regime of lubrication occurs. If the velocity decreases even further and only an ultra-thin lubricant layer composed of a few molecules remain, boundary lubrication occurs. In certain instances, a boundary mode of lubrication is therefore indicated by a friction coefficient (ratio of the measured frictional force between two contacting surfaces in relative motion to the applied normal force) during steady sliding being invariant with factors that influence formation of a fluid film, such as relative sliding velocity and axial load.

For certain tissues in the body, such as articular cartilage, it has been concluded that boundary lubrication occurs, and is complemented by fluid pressurization and other mechanisms. Use of agents for intravaginal boundary lubrication has not been previously pursued, however, because, e.g., the dominant modes of intravaginal lubrication have been assumed to be hydrodynamic and elastohydrodynamic. Moreover, treatments for compromised vaginal lubricating ability have traditionally focused on viscous fluid phase lubrication or hydration with long chain polymers such as polycarbophils, polyethylene glycols, and glycerin.

In boundary lubrication, load is supported by surface-to-surface contact, and the associated frictional properties are determined by lubricant surface molecules. In certain instances, this mode may be important because the opposing tissue surface make contact over ~10% of the total area, and this may be where most of the friction occurs. Furthermore, in some instances, with increasing loading time and dissipation of hydrostatic pressure, lubricant-coated surfaces bear an increasingly higher portion of the load relative to pressurized fluid, and consequently, this mode can become increasingly dominant. In certain instances, boundary lubrication mitigates stick-slip, and is therefore manifest as decreased resistance both to steady motion and the start-up of motion. In some instances, the latter situation is relevant to load bearing surfaces after prolonged compressive loading (e.g., sitting or standing in vivo). Typical wear patterns of articular surfaces, such as in cartilage, also illustrate that in some instances, boundary lubrication is important for the protection and maintenance of the tissue structure. In some instances, the loading of the vaginal epithelium is subject to (e.g., dominated by) shear forces, with intercourse generating significant stress upon surface cells. Moreover, in disease states that down regulate production of lubricants within the vagina or act to atrophy epithelial cells, routine, non-intercourse derived shear stress may also pose a strong degradatory and inflammatory risk. Severe atrophy or iatrogenically caused dryness from cancer treatments such as tamoxifen, antihistamines, treatments for urinary tract infections, anti-depressants, or high blood pressure medication may also make normal levels of shear stress, independent of intercourse, painful.

In some instances, the accumulation of PRG4 within fluid between articulating surfaces, as well as its propensity to spontaneously bind to tissue matrix, contribute to PRG4's boundary lubricating ability.

In certain embodiments described herein, we disclose that proteoglycan 4 (PRG4) plays a role as a boundary lubricant along the walls of the vaginal cavity. In some embodiments, this glycoprotein (PRG4) protects vaginal surfaces against frictional forces, cell adhesion and/or protein deposition. Any one or more of various native and recombinant lubricin proteins and isoforms are utilized in various embodiments described herein. For instance, U.S. Pat. Nos. 5,326,558; 6,433,142; 7,030,223, and 7,361,738 disclose a family of human megakaryocyte stimulating factors (MSFs), each of which is incorporated herein for such disclosure. U.S. Pat. Nos. 6,960,562 and 6,743,774 also disclose a lubricating polypeptide, tribonectin, comprising a substantially pure fragment of MSF, each of which is incorporated herein for such disclosure.

Provided in certain embodiments herein, is a method for treating vaginal lubrication deficiency (e.g., vaginal boundary lubrication deficiency) (or improving vaginal lubrication), or symptoms associated therewith, in an individual in need thereof comprising topically administering to the vaginal surface of the individual a pharmaceutical composition comprising a therapeutically effective amount of PRG4 protein. Also provided in some embodiments herein are pharmaceutical compositions comprising PRG4 protein in a vaginally acceptable formulation (vaginally acceptable defined as formulations that do not cause undue discomfort, pain, allergy, inflammation, or heat), e.g., for treating vaginal lubrication deficiency (e.g., vaginal boundary lubrication deficiency) (or improving vaginal lubrication). In some embodiments, a vaginally acceptable formulation comprises a demulcent, an astringent, an emollient, or combinations thereof. In some embodiments the composition is used to treat or coat a prophylactic device or administered via a eluting implantable device (e.g. an eluting ring). In some embodiments, such administration is achieved by administering an eluting implantable device, the implantable device then eluting a therapeutically effective amount of PRG4. In certain embodiments, an eluting implantable device is utilized to provide a prolonged therapy.

Provided in some embodiments herein are pharmaceutical compositions, and methods of use thereof, for treating a deficiency in vaginal lubrication at the vaginal epithelium (e.g. a deficiency of, such as decreased or undesirable vaginal boundary lubrication). A pharmaceutical composition of certain embodiments of the present invention comprises an isolated or purified PRG4 protein (e.g., suspended in a vaginally acceptable balanced salt solution) in combination with one or more agents selected from the group consisting of a demulcent, excipient, astringent, vasoconstrictor, and emollient. In some embodiments, any pharmaceutical composition provided herein further comprises one or more additional therapeutic agents selected from the group consisting of sodium hyaluronate, surface active phospholipids, and electrolytes in a pharmaceutically acceptable carrier for topical administration.

The present invention provides, in certain embodiments, a novel approach to manage vaginal lubrication, including the therapeutic replenishment and enrichment of boundary lubricant molecules at the vaginal surface. The present invention provides that PRG4 is synthesized by vaginal epithelial cells and then secreted onto the vaginal surface. Furthermore, the present invention provides that PRG4 serves an analogous role on the vaginal surface and protects vaginal epithelial surfaces against significant shear forces generated during intercourse, or in disease states or other iatrogenic factors that compromise its boundary lubricating abilities.

There is a need to manage vaginal lubrication and to protect the vaginal epithelium against shear forces (including significant shear forces) and discomfort generated from the undesirable conditions described herein, including, by way of non-limiting example, vaginal atrophy, dyspareunia, Sjögren's syndrome, androgen deficiency, estrogen deficiency, estrogen replacement therapy, allergy, chronic inflammation, menopause, premature menopause, chemotherapy, breastfeeding, surgical removal of the ovaries before menopause, genital lichen sclerosis, vulvodynia, bacterial vaginosis, herpes, candida, psoriasis, contact dermatitis, condylomata, side effects of medications and aging. Symptoms or indications of vaginal lubrication deficiency include, by way of non-limiting example, vaginal dryness, vaginal itch or a burning sensation, painful sexual intercourse, and light vaginal bleeding after intercourse.

A deficiency in vaginal lubrication and symptoms associated therewith can be determined by any suitable method. In some instances, a deficiency in vaginal lubrication and symptoms associated therewith is defined either qualitatively (e.g., a feeling of low lubrication, discomfort, vaginal dryness, vaginal itch or a burning sensation, painful sexual intercourse, and light vaginal bleeding after intercourse etc.) or quantitatively (e.g., measured through mechanical, biochemical, electrical, optical or other methods of quantitative assays).

In certain embodiments, the present invention provides compositions and methods for modulation of PRG4 regulation on the vaginal surface to promote favorable conditions for proper boundary lubrication. A pharmaceutical composition of certain embodiments of the present invention comprises and isolated or purified PRG4 protein in combination with one or more of the following pharmaceutical agents, including, a therapeutically effective amount of an androgen or androgen analogue, estrogen or estrogen analogue, oestradiol, selective androgen receptor modulator, selective estrogen receptor modulator, estrogen antagonist, aromatase inhibitor, antiprotease, proinflammatory cytokine antagonist, cytokine release inhibitor, antiinflammatory cytokine (e.g. TGF-β), antiinflammatory agent (e.g. cyclosporine A, omega 3 and 6 fatty acids), NF-κB inhibitor, or proteasome inhibitor, hyaluronic acid, neutral or polar lipids, fatty acids, progesterone, follicle stimulating hormone, leutinizing hormone, or other molecules to promote epithelial growth and pharmaceutically acceptable carriers for topical use.

In one embodiment, the androgen or androgen analogue is selected from the group consisting of a 17α-methyl-17β-hydroxy-2-oxa-5α-androstan-3-one derivative, a nitrogen-substituted androgen, a testosterone derivative (i.e., a testosterone central ring molecule with modified sidechains, such as addition or subtraction of amino, hydroxyl, hydrogen, methyl, oxygen or other groups to affect stability or solubility, as well as addition or subtraction of saturation within the ring structure to modify stability or solubility), is a 4,5α-dihydrotestosterone derivative, a 19-nortestosterone derivative, a 17β-hydroxy-5α-androstane derivative containing a ring A unsaturation, and a structural subclass of androgens comprising androgenic compounds with unusual structural features, and a phosphate buffered saline or a carrier substance such as hyaluronate for topical use. Any pharmaceutically acceptable carrier and/or excipients suitable for topical use are within the scope of the invention.

In another embodiment, the selective androgen receptor modulators (SARMs) are selected from a group consisting of aryl-propionamide (e.g. S-3-(4-acetylamino-phenoxy)-2-hydroxy-2-methyl-N-(4-nitro-3-trifluoromethyl-phenyl)-propionamide [S-4], or S-3-(4-fluorophenoxy)-2-hydroxy-2-methyl-N-(4-nitro-3-trifluoromethyl-phenyl)-propionamide [S-1]), bicyclic hydantoin, quinoline, and tetrahydroquinoline analogues that have in-vivo androgenic and anabolic activity of a non-steroidal ligand for the androgen receptor.

In yet another embodiment, the selective estrogen receptor modulators (SERMs) are non-steroidal ligands of the estrogen receptor that are capable of inducing a number of conformational changes in the receptor and eliciting a variety of distinct biologic profiles. Preferably, the SERMs are those that prevent estrogen-induced inflammation in vaginal surface tissues. In yet certain preferred embodiment, the estrogen antagonists are steroidal or non-steroidal compounds regardless of receptor affinities.

In one embodiment, the proinflammatory cytokine antagonist is selected from the group consisting of anti-TNFα antibody, soluble TNFα receptor, and IL-1 receptor antagonist.

In yet another embodiment, the estrogen or progesterone include commercially available hormone replacement therapies, including, Estrace, Premarin and Estring.

In some embodiments, isolated or purified PRG4 is formulated for vaginal use, e.g., with a vaginally acceptable excipient. In certain embodiments, compositions described herein are formulated to deliver an effective amount of PRG4 to the vagina of an individual in need thereof. In some embodiments, the composition is formulated as a topical formulation, such as a cream, a salve, a solution, a suspension, a paste, an ointment, or the like. Administration of such a composition is achieved in any suitable manner, such as by enema, douche, hand, spray, suppository, impregnated device, applicator, or the like. In various embodiments, administration is performed in an area as needed, e.g., the exterior surface of the vagina, interior surface of the vagina, or portions and/or combinations thereof. In some embodiments, the PRG4 is formulated for extended or prolonged release, such as in a suppository, or in tampon embedded with an extended release formulation.

Coated Prophylactics

In certain embodiments of the present invention provide a prophylactic comprising PRG4 or any PRG4 pharmaceutical composition. Also, described herein are methods of treating a prophylactic comprising depositing (e.g., attaching, coating, or the like) PRG4 or any PRG4 pharmaceutical composition described herein on the surface of the prophylactic. Deposition of the PRG4 on the prophylactic is achieved in any suitable manner, such as coating (e.g., in a suitable composition), attaching by covalent bond, associating through hydrobphobic or ionic interactions, or the like. Also provided herein are other vaginal devices (e.g., tampon) having PRG4 deposited thereon. In some embodiments, deposition of the PRG4 on the device reduces the irritation caused by such a device, particularly in an individual suffering from decreased vaginal lubrication (e.g., decreased vaginal boundary lubrication).

In yet another embodiment further comprising the supplementing the prophylactic with topical administration of an effective amount of PRG4 or any pharmaceutical composition described herein.

A method of providing lubrication during intercourse comprising the topical administration to the vaginal surface, penile surface, of an effective amount of PRG4 or any pharmaceutical composition described herein.

Administration of the PRG4 is achieved in any suitable manner, such as through topical administration, administration with a cream, gel, solution, or any other spreadable composition. In some embodiments, administration is achieved with an implantable device, such as a tampon impregnated with PRG 4 or PRG4 composition. In some embodiments, PRG4 is combined with another personal lubricant, or personal lubricant composition, e.g., a petroleum-based lubricant, such as K-Y Jelly.

In certain embodiments of the present invention provide a personal lubricant that increases the chances of conception by maintaining or increasing the motility of sperm that comes into contact therewith comprised of the application to the vagina, of a patient in need, an effective amount of PRG4 or any pharmaceutical composition described herein. Many commercially available lubricant containing ingredients such as glycerin are spermicidal and impede sperm motility. In some instances, PRG4, a normal component of vaginal fluid, may play a role in maintaining sperm motility and promoting conception. In another embodiment, a personal lubricant or any other composition described herein comprises an additive, e.g., an additive to release nitric oxide such as natural nitric oxide precursors such as amino acids, for example L-Arginine, citrulline and aspartic acid. Such additives may induce a warming effect upon application of the lubricant to the vagina thus increasing vaginal sensation. In addition, the release of nitric oxide may have the effect of maintaining or enhancing sperm motility. As such the inclusion of nitric oxide releasing compounds may increase or maximize the chances of conception.

In one embodiment, the pharmaceutical composition described herein has a pH of 2.4 to 7.8, 5.8 to 7.4; or 6.5 to 7.4.

As used herein, the term "prophylactics" refers to devices used for the prevention of pregnancy, including male and female condoms.

As used herein, the term "PRG4", "PRG4 protein" or "proteoglycan 4" protein, is used interchangeably with the term "lubricin" protein. PRG4 is used herein also to encompass the term megakaryocyte stimulating factor (MSF), that has been accepted for the UCL/HGNC/HUGO Human Gene Nomenclature data base, and superficial zone protein (SZP). The PRG4 or lubricin protein (used interchangeably herein with lubricin proteoglycan) as used herein refers to any isolated or purified native or recombinant lubricin proteins, homologs, functional fragments or motifs, isoforms, and/or mutants thereof. In certain embodiments, the isolated or purified PRG4 protein comprises an amino acid sequence for a human native or recombinant lubricin protein. In other embodiments, the isolated or purified PRG4 protein comprises an amino acid sequence encoded by prg4 gene exons that encode the full length PRG4 protein or isoforms' primary structures. The proteoglycan 4 (prg4) gene contains 12 exons. The PRG4 protein used herein comprises an amino acid sequence encoded by prg4 gene exons 1-12, more preferably, exons 6-12, and most preferably, exons 9-12.

As used herein, the PRG4 protein includes any PRG4 proteins now known, or later described. In certain embodiments, a preferred PRG4 protein amino acid sequence is provided in SEQ ID NO:1. The PRG4 protein shares the primary amino acid structure of any known PRG4 proteins or isoforms with at least 60% homology, preferably 75% homology, more preferably 85%, 90%, 95%, 96%, 97%, 98%, 99% or more homology. In certain embodiments, a preferred PRG4 protein has an average molar mass of between 50 kDa and 400 kDa, comprising one or more biological active portions of the PRG4 protein, or functional fragments, such as a lubricating fragment, or a homolog thereof.

As used herein, the PRG4 protein comprises a biological active portion of the protein. As used herein, a "biologically active portion" of the PRG4 protein includes a functional fragment of a protein comprising amino acid sequences sufficiently homologous to, or derived from, the amino acid sequence of the protein, which includes fewer amino acids than the full length protein, and exhibits at least one activity of the full-length protein. Typically a biologically active portion comprises a functional domain or motif with at least one activity of the protein. A biologically active portion of a protein can be a polypeptide which is, for example, 10, 25, 50, 100, 200, or more amino acids in length. In one embodiment, a biologically active portion of the PRG4 protein can be used as a therapeutic agent alone or in combination with other therapeutic agents for treating undesirable or decreased vaginal boundary lubrication.

In yet another embodiment, functional fragments, multimers (e.g., dimers, trimers, tetramers, etc.), homologs or orthologs of PRG4 are used in the oral care composition. Functional fragments and homologs of PRG4 include those with fewer repeats within the central mucin-like KEPAPTT-repeat domain, glycosylated and non-glycosylated forms of the protein, splice variants, recombinant forms, and the like. A lubricating fragment of PRG4 exhibits at least 20%, 30%, 40%, 50%, 60%, 70%, 80%, 90%, or 95% of the lubricating effect of human PRG4, as measured qualitatively, mechanically, optically, electrically, or by biochemical assay.

The nucleic acid and amino acid sequences of several native and recombinant PRG4 or lubricin proteins, and characterization of the PRG4 proteins and various isoforms are disclosed in, for instance, U.S. Pat. Nos. 5,326,558; 6,433, 142; 7,030,223; 7,361,738 to Turner et al., and U.S. Pat. Nos. 6,743,774 and 6,960,562 to Jay et al., U.S. Publication No. 20070191268 to Flannery et al. also discloses recombinant PRG4 or lubricin molecules useful in the present invention.

Methods for isolation, purification, and recombinant expression of a PRG4 protein are well known in the art. In certain embodiments, the method starts with cloning and isolating mRNA and cDNA encoding PRG4 proteins or isoforms using standard molecular biology techniques, such as PCR or RT-PCR. The isolated cDNA encoding the PRG4 protein or isoform is then cloned into an expression vector, and further transformed and expressed in a host cell for producing recombinant PRG4 protein.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant" also encompasses the ligation of nucleic acids having various coding regions or domains or promoter sequences from different sources into an expression cassette or vector for expression of, e.g., inducible or constitutive expression of a fusion protein comprising an active domain of the PRG4 gene and a nucleic acid sequence amplified using a primer of the invention.

In certain embodiments, the PRG4 protein encoding nucleic acid may contain one or more mutations, deletions, or insertions. In such embodiments, the PRG4 protein encoding nucleic acid is at least 60% homology, preferably 75% homology, more preferably 85%, 90%, 95%, 96%, 97%, 98%, 99%, or more homology, to a wild type PRG4 protein encoding nucleic acid.

As used herein, the term "'cDNAs" includes DNA that is complementary to mRNA molecules present in a cell or organism mRNA that can be converted into cDNA with an enzyme such as reverse transcriptase. In certain embodiments, the cDNA encoding PRG4 protein is isolated from PRG4 mRNA expressed in human corneal or conjunctival epithelial cells using an RT-PCR method well known in the art.

As used herein, the terms "polynucleotide," "nucleic acid/nucleotide," and "oligonucleotide" are used interchangeably, and include polymeric forms of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, DNA, cDNA, genomic DNA, recombinant polynucleotides, branched polynucleotides, plasmids, vectors, isolated DNA of any sequence, isolated RNA of any sequence, nucleic acid probes, and primers. Polynucleotides may be naturally-occurring, synthetic, recombinant or any combination thereof.

A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, any embodiment of this invention that is a polynucleotide encompasses both the double-stranded form and each of two complementary single-stranded forms known or predicted to make up the double-stranded form.

As used herein, the term "polynucleotide sequence" is the alphabetical representation of a polynucleotide molecule. A polynucleotide is composed of a specific sequence of four nucleotide bases: adenine (A); cytosine (C); guanine (G); thymine (T); and uracil (U) in place of thymine when the polynucleotide is RNA, instead of DNA. This alphabetical representation can be inputted into databases in a computer and used for bioinformatics applications such as, for example, functional genomics and homology searching.

As used herein, the term "isolated polynucleotide/cDNA" includes polynucleotide molecules which are separated from other polynucleotide molecules which are present in the natural source of the polynucleotide. For example, with regard to genomic DNA, the term "isolated" includes polynucleotide molecules which are separated from the chromosome with which the genomic DNA is naturally associated. Preferably, an "isolated" polynucleotide is free of sequences which naturally flank the polynucleotide (i.e., sequences located at the 5' and 3' ends of the polynucleotide of interest) in the genomic DNA of the organism from which the polynucleotide is derived. For example, in various embodiments, the isolated polynucleotide molecule encoding the PRG4 protein used in the invention can contain less than about 5 kb, 4 kb, 3 kb, 2 kb, 1 kb, 0.5 kb or 0.1 kb of nucleotide sequences which naturally flank the polynucleotide molecule in genomic DNA of the cell from which the polynucleotide is derived. Moreover, an "isolated" polynucleotide molecule, such as a cDNA molecule, can be substantially free of other cellular material or culture medium when produced by recombinant techniques, or substantially free of chemical precursors or other chemicals when chemically synthesized.

As used herein, a "gene" includes a polynucleotide containing at least one open reading frame that is capable of encoding a particular polypeptide or protein after being transcribed and translated. Any of the polynucleotide sequences described herein may also be used to identify larger fragments or full-length coding sequences of the gene with which they are associated. Methods of isolating larger fragment sequences are known to those of skill in the art. As used herein, a "native or naturally-occurring" polynucleotide molecule includes, for example, an RNA or DNA molecule having a nucleotide sequence that occurs in nature (e.g., encodes a natural protein).

As used herein, the term "polypeptide" or "protein" is interchangeable, and includes a compound of two or more subunit amino acids, amino acid analogs, or peptidomimetics. The subunits may be linked by peptide bonds. In another embodiment, the subunit may be linked by other bonds, e.g., ester, ether, etc. As used herein, the term "amino acid" includes either natural and/or unnatural or synthetic amino acids, including glycine and both the D or L optical isomers, and amino acid analogs and peptidomimetics. A peptide of three or more amino acids is commonly referred to as an oligopeptide. Peptide chains of greater than three or more amino acids are referred to as a polypeptide or a protein.

In certain embodiments, the PRG4 protein used herein refers to PRG4 proteins or various homologs or isoforms thereof, that are naturally or recombinantly expressed in humans or other host cells. As used herein, "express" or "expression" includes the process by which polynucleotides are transcribed into RNA and/or translated into polypeptides. If the polynucleotide is derived from genomic DNA, expression may include splicing of the RNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described below for constructing vectors in general. As used herein, the term "vector" includes a self-replicating nucleic acid molecule that transfers an inserted polynucleotide into and/or between host cells. The term is intended to include vectors that function primarily for insertion of a nucleic acid molecule into a cell, replication vectors that function primarily for the replication of nucleic acid and expression vectors that function for transcription and/or translation of the DNA or RNA. Also intended are vectors that provide more than one of the above function.

As used herein, a "host cell" is intended to include any individual cell or cell culture which can be, or has been, a recipient for vectors or for the incorporation of exogenous polynucleotides and/or polypeptides. It is also intended to include progeny of a single cell. The progeny may not necessarily be completely identical (in morphology or in genomic or total DNA complement) to the original parent cell due to natural, accidental, or deliberate mutation. The cells may be prokaryotic or eukaryotic, and include but are not limited to bacterial cells, yeast cells, insect cells, animal cells, and mammalian cells, including but not limited to murine, rat, simian or human cells. As used herein, a "host cell" also includes genetically modified cells. The term "genetically modified cells" includes cells containing and/or expressing a foreign or exogenous gene or polynucleotide sequence which in turn modifies the genotype or phenotype of the cell or its progeny. "Genetically modified" also includes a cell containing or expressing a gene or polynucleotide sequence which has been introduced into the cell. For example, in this embodiment, a genetically modified cell has had introduced a gene which gene is also endogenous to the cell. The term "genetically modified" also includes any addition, deletion, or disruption to a cell's endogenous nucleotides. As used herein, a "host cell" can be any cells that express a human PRG4 protein.

As used herein, "homologs" are defined herein as two nucleic acids or peptides that have similar, or substantially identical, nucleic acids or amino acid sequences, respectively. The term "homolog" further encompasses nucleic acid molecules that differ from one of the nucleotide sequences due to degeneracy of the genetic code and thus encodes the same amino acid sequences. In one of the preferred embodiments, homologs include allelic variants, orthologs, paralogs, agonists, and antagonists of nucleic acids encoding the PRG4 protein (e.g., SEQ ID NO:1, see, e.g., FIG. 3).

As used herein, the term "orthologs" refers to two nucleic acids from different species, but that have evolved from a common ancestral gene by speciation. Normally, orthologs encode peptides having the same or similar functions. In particular, orthologs of the invention will generally exhibit at least 80-85%, more preferably 85-90% or 90-95%, and most preferably 95%, 96%, 97%, 98%, or even 99% identity, or 100% sequence identity, with all or part of the amino acid sequence of any known PRG4 proteins (e.g., SEQ ID NO:1), isoforms, or analogs thereof, and will exhibit a function similar to these peptides. As also used herein, the term "paralogs" refers to two nucleic acids that are related by duplication within a genome. Paralogs usually have different functions, but these functions may be related.

To determine the percent sequence identity of two amino acid sequences, the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence is occupied by the same amino acid residue as the corresponding position in the other sequence, then the molecules are identical at that position. The same type of comparison can be made between two nucleic acid sequences. The percent sequence identity between the two sequences is a function of the number of identical positions shared by the sequences (i.e., percent sequence identity=numbers of identical positions/total numbers of positions×100). Preferably, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence of any known PRG4 protein (e.g., SEQ ID NO:1).

In certain embodiments, an isolated nucleic acid homolog encoding the PRG4 protein comprises a nucleotide sequence which is at least about 40-60%, preferably at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence encoding amino acid sequences of such PRG4 protein (e.g., SEQ ID NO:1).

The determination of the percent sequence identity between two nucleic acid or peptide sequences is well known in the art. For instance, the Vector NTI 6.0 (PC) software package (InforMax, Bethesda, Md.) to determine the percent sequence identity between two nucleic acid or peptide sequences can be used. In this method, a gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

Furthermore, the PRG4 protein used herein includes PRG4 protein encoded by a polynucleotide that hybridizes to the polynucleotide encoding PRG4 protein under stringent conditions. As used herein, "hybridization" includes a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under different stringent conditions. The present invention includes polynucleotides capable of hybridizing under reduced stringency conditions, more preferably stringent conditions, and most preferably highly stringent conditions, to polynucleotides encoding PRG4 protein described herein. As used herein, the term "stringent conditions" refers to hybridization overnight at 60° C. in 10×Denhart's solution, 6×SSC, 0.5% SDS, and 100 mg/ml denatured salmon sperm DNA. Blots are washed sequentially at 62° C. for 30 minutes each time in 3×SSC/0.1% SDS, followed by 1×SSC/0.1% SDS, and finally 0.1× SSC/0.1% SDS. As also used herein, in certain embodiments, the phrase "stringent conditions" refers to hybridization in a 6×SSC solution at 65° C. In other embodiments, "highly stringent conditions" refer to hybridization overnight at 65° C. in 10×Denhart's solution, 6×SSC, 0.5% SDS and 100 mg/ml denatured salmon sperm DNA. Blots are washed sequentially at 65° C. for 30 minutes each time in 3×SSC/0.1% SDS, followed by 1×SSC/0.1% SDS, and finally 0.1× SSC/0.1% SDS. Methods for nucleic acid hybridizations are well known in the art. Accordingly, the PRG4 proteins encoded by nucleic acids used herein include nucleic acid having at least 60% homology, preferably 75% homology, more preferably 85%, more preferably 90%, most preferably 95%, 96%, 97%, 98%, 99% homology to a polynucleotide sequence that encodes a human PRG4 protein (e.g., SEQ ID NO:1) or a specific isoform or homolog thereof.

Moreover, the PRG4 proteins used herein can also be chimeric protein or fusion protein. As used herein, a "chimeric protein" or "fusion protein" comprises a first polypeptide operatively linked to a second polypeptide. Chimeric proteins may optionally comprise a third, fourth or fifth or other polypeptide operatively linked to a first or second polypeptide. Chimeric proteins may comprise two or more different polypeptides. Chimeric proteins may comprise multiple copies of the same polypeptide. Chimeric proteins may also comprise one or more mutations in one or more of the polypeptides. Methods for making chimeric proteins are well known in the art. In certain embodiments of the present invention, the chimeric protein is a chimera of PRG4 protein with other PRG4 protein isoforms.

As used herein, an "isolated" or "purified" protein, polynucleotide or molecule means removed from the environment in which they naturally occur, or substantially free of cellular material, such as other contaminating proteins from the cell or tissue source from which the protein polynucleotide or molecule is derived, or substantially free from chemical precursors or other chemicals when chemically synthesized. The language "substantially free of cellular material" includes preparations separated from cellular components of the cells from which it is isolated or recombinantly produced or synthesized. In certain embodiments, the language "substantially free of cellular material" includes preparations of a PRG4 protein having less than about 30% (by dry weight) of other proteins (also referred to herein as a "contaminating protein"), more preferably less than about 20%, still more preferably less than about 10%, and most preferably less than about 5% of other proteins. When the protein or polynucleotide is recombinantly produced, it is also preferably substantially free of culture medium, i.e., culture medium represents less than about 20%, more preferably less than about 10%, and most preferably less than about 5% of the volume of the preparation of the protein of interest.

EXAMPLES

Example 1

Treatment of Deficient Vaginal Boundary Lubrication In Vivo

A 65-year old post-menopausal patient complains of vaginal surface irritation, burning during urination, dyspareunia, intermittent light bleeding after intercourse, and periodic vaginal discharge is examined, ruled out to have active infections, and is determined to have atrophic vaginitis. In particular, the pelvic examination reveals the appearance of thin, pale vaginal walls.

The patient is administered a weekly intravaginal PRG4/17β-oestradiol suppository that provides doses of 100 μg/mL PRG4 and 1 μg of 17β-oestradiol, which although far lower in total concentration than typical oestradiol therapies, is delivered directly to the vaginal wall by PRG4 co-transport. Endometrial histopathology during annual follow-up visits will reveal, in certain instances, improved labial and vulvar fullness, flushed urethral and vaginal epithelium, and/or symptoms (e.g., wherein no symptoms remain).

Example 2

Treatment of Deficient Vaginal Boundary Lubrication in a Cancer Patient

A 60-year old menopausal breast cancer patient who recently finishes a course of tamoxifen chemotherapy, presents with an inflamed vaginal epithelium, with patchy erythema, petechiae, and increased friability, in addition to a small vulvar lesion. In addition, a vaginal ultrasound reveals a thin endometrium of around 4 mm in width. No evidence of trichomonas, candida or other bacteria is found. Papanicolaou smears reveal immature parabasal squamous epithelial cells with enlarged nuclei in a background of amorphous basophilic granular debris and inflammatory exudate.

The patient is administered to the vagina a daily dose of buffered PRG4 gel at 200 μg/mL. At the 6-month follow up Papanicolaou smears are performed to demonstrate squamous cells from the superficial and intermediate layers of the vaginal epithelium. In some instances, unlike the original visit, many of the cells will exhibit abundant cytoplasm with a low nuclear-cytoplasmic ratio. In certain instances, most nuclei will be condensed, and there will be evidence of a properly keratinized, pink cytoplasm. In some instances, the patient will exhibit improved tissue elasticity and less inflammation. In certain instances, the symptoms will be completely alleviated, or improved from severe to tolerable.

What is claimed is:

1. A method of treating decreased vaginal boundary lubrication or a disease or condition associated therewith or of improving vaginal boundary lubrication, the method comprising topically administering to a vaginal surface of a subject in need thereof a therapeutically effective amount of isolated or purified lubricin or a lubricating fragment, multimer, or homolog thereof sufficient to improve vaginal boundary lubrication.

2. The method of claim 1, wherein the disease or condition associated with decreased vaginal boundary lubrication is vaginal atrophy, dyspareunia, Sjogren's syndrome, menopause, androgen deficiency, estrogen deficiency, estrogen replacement therapy, allergy, chronic inflammation, menopause, premature menopause, chemotherapy, breastfeeding, surgical removal of the ovaries before menopause, genital lichen sclerosis, vulvodynia, bacterial vaginosis, herpes, candida, psoriasis, contact dermatitis, condylomata, or side effects of medications and aging.

3. The method of claim 1, wherein the lubricin or lubricating fragment, multimer, or homolog thereof is formulated in a gel, an aqueous osmotically balanced salt solution, a multiphasic emulsion, or a slow- or extended-release device.

4. The method of claim 1, wherein the therapeutically effective amount of lubricin or lubricating fragment, multimer, or homolog thereof is in a concentration of 10-10,000 μg/mL.

5. The method of claim 1, wherein the lubricin or lubricating fragment, multimer, or homolog thereof has an average molar mass of between 50 kDa and 400 kDa.

6. The method of claim 1, wherein the lubricin or lubricating fragment, multimer, or homolog thereof is a recombinant lubricin, or lubricating fragment, multimer, or homolog thereof, or a purified naturally occurring lubricin or lubricating fragment, multimer, or homolog thereof.

7. The method of claim 1, further comprising administering a therapeutic agent selected from the group consisting of an androgen, androgen analogue, selective androgen receptor modulator, selective estrogen receptor modulator, estrogen antagonist, aromatase inhibitor, antiprotease, proinflammatory cytokine antagonist, cytokine release inhibitor, anti-inflammatory cytokine, anti-inflammatory agent, NF-κB inhibitor, proteasome inhibitor, hyaluronic acid, neutral lipids, polar lipids, fatty acids, estrogen, estrogen analogue, oestradiol, progesterone, follicle stimulating hormone, luteinizing hormone, sodium hyaluronate, and nitric oxide.

8. The method of claim 7, wherein said androgen or androgen analogue is a 17α-methyl-17β-hydroxy-2-oxa-5α-androstan-3-one derivative, a testosterone derivative, 4,5α-dihydrotestosterone derivative, a 17β-hydroxy-5α-androstane derivative containing a ring A unsaturation, a 19-nortestosterone derivative, a nitrogen-substituted androgen, or a combination thereof.

9. The method of claim 7, wherein said selective androgen receptor modulator is an aryl-propionamide compound, a bicyclic hydantoin analogue, a quinoline analogue, or a tetrahydroquinoline analogue.

10. The method of claim 7, wherein said proinflammatory cytokine antagonist is an anti-TNFα antibody, a soluble TNF α receptor, or an IL-1 receptor antagonist.

11. The method of claim 7, wherein said anti-inflammatory agent is cyclosporine A, omega 3 fatty acids, or omega 6 fatty acids.

12. The method of claim 7, wherein the composition comprises sodium hyaluronate or hyaluronic acid in a concentration of 10-100,000 μg/mL.

13. The method of claim 7, wherein the composition comprises sodium hyaluronate or hyaluronic acid in a concentration of 500-5,000 μg/mL.

14. A method of providing lubrication during intercourse or promoting conception comprising topically administering to a vaginal surface, a penile surface, or a combination thereof an effective amount of an isolated or purified lubricin or a lubricating fragment, multimer, or homolog thereof sufficient to improve vaginal boundary lubrication.

15. A method of treating decreased vaginal boundary lubrication or a disease or condition associated therewith or of improving vaginal boundary lubrication, the method comprising topically administering to a vaginal surface of a subject in need thereof a therapeutically effective amount of isolated or purified lubricin or a lubricating fragment, multimer, or homolog thereof sufficient to improve vaginal boundary lubrication and a therapeutic agent selected from the group consisting of an androgen, androgen analogue, selective androgen receptor modulator, selective estrogen receptor modulator, aromatase inhibitor, antiprotease, cytokine release inhibitor, NF-κB inhibitor, proteasome inhibitor, neutral lipids, polar lipids, fatty acids, estrogen, estrogen analogue, oestradiol, progesterone, follicle stimulating hormone, luteinizing hormone, and nitric oxide.

* * * * *

```
SEQUENCE LISTING

<160> NUMBER OF SEQ ID NOS: 3

<210> SEQ ID NO 1
<211> LENGTH: 1404
<212> TYPE: PRT
<213> ORGANISM: Homo sapiens

<400> SEQUENCE: 1

Met Ala Trp Lys Thr Leu Pro Ile Tyr Leu Leu Leu Leu Ser Val
1               5                  10                  15

Phe Val Ile Gln Gln Val Ser Ser Gln Asp Leu Ser Ser Cys Ala Gly
                20                  25                  30

Arg Cys Gly Glu Gly Tyr Ser Arg Asp Ala Thr Cys Asn Cys Asp Tyr
            35                  40                  45

Asn Cys Gln His Tyr Met Glu Cys Cys Pro Asp Phe Lys Arg Val Cys
    50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
                100                 105                 110

Pro Pro Ser Ser Lys Lys Ala Pro Pro Ser Gly Ala Ser Gln Thr
            115                 120                 125

Ile Lys Ser Thr Thr Lys Arg Ser Pro Lys Pro Asn Lys Lys Lys
        130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser
                165                 170                 175

Ser Thr Ile Arg Lys Ile Lys Ser Ser Lys Asn Ser Ala Ala Asn Arg
            180                 185                 190
```

-continued

```
Glu Leu Gln Lys Lys Leu Lys Val Lys Asp Asn Lys Lys Asn Arg Thr
            195                 200                 205
Lys Lys Lys Pro Thr Pro Lys Pro Pro Val Val Asp Glu Ala Gly Ser
210                 215                 220
Gly Leu Asp Asn Gly Asp Phe Lys Val Thr Thr Pro Asp Thr Ser Thr
225                 230                 235                 240
Thr Gln His Asn Lys Val Ser Thr Ser Pro Lys Ile Thr Thr Ala Lys
            245                 250                 255
Pro Ile Asn Pro Arg Pro Ser Leu Pro Pro Asn Ser Asp Thr Ser Lys
            260                 265                 270
Glu Thr Ser Leu Thr Val Asn Lys Glu Thr Thr Val Glu Thr Lys Glu
            275                 280                 285
Thr Thr Thr Thr Asn Lys Gln Thr Ser Thr Asp Gly Lys Glu Lys Thr
            290                 295                 300
Thr Ser Ala Lys Glu Thr Gln Ser Ile Glu Lys Thr Ser Ala Lys Asp
305                 310                 315                 320
Leu Ala Pro Thr Ser Lys Val Leu Ala Lys Pro Thr Pro Lys Ala Glu
            325                 330                 335
Thr Thr Thr Lys Gly Pro Ala Leu Thr Thr Pro Lys Glu Pro Thr Pro
            340                 345                 350
Thr Thr Pro Lys Glu Pro Ala Ser Thr Thr Pro Lys Glu Pro Thr Pro
            355                 360                 365
Thr Thr Ile Lys Ser Ala Pro Thr Thr Pro Lys Glu Pro Ala Pro Thr
            370                 375                 380
Thr Thr Lys Ser Ala Pro Thr Thr Pro Lys Glu Pro Ala Pro Thr Thr
385                 390                 395                 400
Thr Lys Glu Pro Ala Pro Thr Thr Pro Lys Glu Pro Ala Pro Thr Thr
            405                 410                 415
Thr Lys Glu Pro Ala Pro Thr Thr Lys Ser Ala Pro Thr Thr Pro
            420                 425                 430
Lys Glu Pro Ala Pro Thr Thr Pro Lys Lys Pro Ala Pro Thr Thr Pro
            435                 440                 445
Lys Glu Pro Ala Pro Thr Thr Pro Lys Glu Pro Thr Pro Thr Thr Pro
450                 455                 460
Lys Glu Pro Ala Pro Thr Thr Lys Glu Pro Ala Pro Thr Thr Pro Lys
465                 470                 475                 480
Glu Pro Ala Pro Thr Ala Pro Lys Lys Pro Ala Pro Thr Thr Pro Lys
            485                 490                 495
Glu Pro Ala Pro Thr Thr Pro Lys Glu Pro Ala Pro Thr Thr Thr Lys
            500                 505                 510
Glu Pro Ser Pro Thr Thr Pro Lys Glu Pro Ala Pro Thr Thr Thr Lys
            515                 520                 525
Ser Ala Pro Thr Thr Thr Lys Glu Pro Ala Pro Thr Thr Lys Ser
530                 535                 540
Ala Pro Thr Thr Pro Lys Glu Pro Ser Pro Thr Thr Lys Glu Pro
545                 550                 555                 560
Ala Pro Thr Thr Pro Lys Glu Pro Ala Pro Thr Thr Pro Lys Lys Pro
            565                 570                 575
Ala Pro Thr Thr Pro Lys Glu Pro Ala Pro Thr Thr Pro Lys Glu Pro
            580                 585                 590
Ala Pro Thr Thr Lys Lys Pro Ala Pro Thr Thr Pro Lys Glu Pro
            595                 600                 605
Ala Pro Thr Thr Pro Lys Glu Thr Ala Pro Thr Thr Pro Lys Lys Leu
```

```
                    610                 615                 620
Thr Pro Thr Thr Pro Glu Lys Leu Ala Pro Thr Thr Pro Glu Lys Pro
625                 630                 635                 640

Ala Pro Thr Thr Pro Glu Glu Leu Ala Pro Thr Thr Pro Glu Glu Pro
                    645                 650                 655

Thr Pro Thr Thr Pro Glu Glu Pro Ala Pro Thr Thr Pro Lys Ala Ala
                660                 665                 670

Ala Pro Asn Thr Pro Lys Glu Pro Ala Pro Thr Thr Pro Lys Glu Pro
            675                 680                 685

Ala Pro Thr Thr Pro Lys Glu Pro Ala Pro Thr Thr Pro Lys Glu Thr
690                 695                 700

Ala Pro Thr Thr Pro Lys Gly Thr Ala Pro Thr Thr Leu Lys Glu Pro
705                 710                 715                 720

Ala Pro Thr Thr Pro Lys Lys Pro Ala Pro Lys Glu Leu Ala Pro Thr
                725                 730                 735

Thr Thr Lys Glu Pro Thr Ser Thr Thr Cys Asp Lys Pro Ala Pro Thr
            740                 745                 750

Thr Pro Lys Gly Thr Ala Pro Thr Thr Pro Lys Glu Pro Ala Pro Thr
        755                 760                 765

Thr Pro Lys Glu Pro Ala Pro Thr Thr Pro Lys Gly Thr Ala Pro Thr
    770                 775                 780

Thr Leu Lys Glu Pro Ala Pro Thr Thr Pro Lys Lys Pro Ala Pro Lys
785                 790                 795                 800

Glu Leu Ala Pro Thr Thr Thr Lys Gly Pro Thr Ser Thr Thr Ser Asp
                805                 810                 815

Lys Pro Ala Pro Thr Thr Pro Lys Glu Thr Ala Pro Thr Thr Pro Lys
            820                 825                 830

Glu Pro Ala Pro Thr Thr Pro Lys Lys Pro Ala Pro Thr Thr Pro Glu
        835                 840                 845

Thr Pro Pro Pro Thr Thr Ser Glu Val Ser Thr Pro Thr Thr Thr Lys
    850                 855                 860

Glu Pro Thr Thr Ile His Lys Ser Pro Asp Glu Ser Thr Pro Glu Leu
865                 870                 875                 880

Ser Ala Glu Pro Thr Pro Lys Ala Leu Glu Asn Ser Pro Lys Glu Pro
                885                 890                 895

Gly Val Pro Thr Thr Lys Thr Pro Ala Ala Thr Lys Pro Glu Met Thr
                900                 905                 910

Thr Thr Ala Lys Asp Lys Thr Glu Arg Asp Leu Arg Thr Thr Pro
            915                 920                 925

Glu Thr Thr Thr Ala Ala Pro Lys Met Thr Lys Glu Thr Ala Thr Thr
930                 935                 940

Thr Glu Lys Thr Thr Glu Ser Lys Ile Thr Ala Thr Thr Gln Val
945                 950                 955                 960

Thr Ser Thr Thr Thr Gln Asp Thr Thr Pro Phe Lys Ile Thr Thr Leu
                965                 970                 975

Lys Thr Thr Thr Leu Ala Pro Lys Val Thr Thr Thr Lys Lys Thr Ile
            980                 985                 990

Thr Thr Thr Glu Ile Met Asn Lys Pro Glu Glu Thr Ala Lys Pro Lys
        995                 1000                1005

Asp Arg Ala Thr Asn Ser Lys Ala Thr Thr Pro Lys Pro Gln Lys
    1010                1015                1020

Pro Thr Lys Ala Pro Lys Lys Pro Thr Ser Thr Lys Lys Pro Lys
    1025                1030                1035
```

-continued

```
Thr Met Pro Arg Val Arg Lys Pro Lys Thr Thr Pro Thr Pro Arg
    1040            1045                1050

Lys Met Thr Ser Thr Met Pro Glu Leu Asn Pro Thr Ser Arg Ile
    1055            1060                1065

Ala Glu Ala Met Leu Gln Thr Thr Thr Arg Pro Asn Gln Thr Pro
    1070            1075                1080

Asn Ser Lys Leu Val Glu Val Asn Pro Lys Ser Glu Asp Ala Gly
    1085            1090                1095

Gly Ala Glu Gly Glu Thr Pro His Met Leu Leu Arg Pro His Val
    1100            1105                1110

Phe Met Pro Glu Val Thr Pro Asp Met Asp Tyr Leu Pro Arg Val
    1115            1120                1125

Pro Asn Gln Gly Ile Ile Ile Asn Pro Met Leu Ser Asp Glu Thr
    1130            1135                1140

Asn Ile Cys Asn Gly Lys Pro Val Asp Gly Leu Thr Thr Leu Arg
    1145            1150                1155

Asn Gly Thr Leu Val Ala Phe Arg Gly His Tyr Phe Trp Met Leu
    1160            1165                1170

Ser Pro Phe Ser Pro Pro Ser Pro Ala Arg Arg Ile Thr Glu Val
    1175            1180                1185

Trp Gly Ile Pro Ser Pro Ile Asp Thr Val Phe Thr Arg Cys Asn
    1190            1195                1200

Cys Glu Gly Lys Thr Phe Phe Phe Lys Asp Ser Gln Tyr Trp Arg
    1205            1210                1215

Phe Thr Asn Asp Ile Lys Asp Ala Gly Tyr Pro Lys Pro Ile Phe
    1220            1225                1230

Lys Gly Phe Gly Gly Leu Thr Gly Gln Ile Val Ala Ala Leu Ser
    1235            1240                1245

Thr Ala Lys Tyr Lys Asn Trp Pro Glu Ser Val Tyr Phe Phe Lys
    1250            1255                1260

Arg Gly Gly Ser Ile Gln Gln Tyr Ile Tyr Lys Gln Glu Pro Val
    1265            1270                1275

Gln Lys Cys Pro Gly Arg Arg Pro Ala Leu Asn Tyr Pro Val Tyr
    1280            1285                1290

Gly Glu Thr Thr Gln Val Arg Arg Arg Phe Glu Arg Ala Ile
    1295            1300                1305

Gly Pro Ser Gln Thr His Thr Ile Arg Ile Gln Tyr Ser Pro Ala
    1310            1315                1320

Arg Leu Ala Tyr Gln Asp Lys Gly Val Leu His Asn Glu Val Lys
    1325            1330                1335

Val Ser Ile Leu Trp Arg Gly Leu Pro Asn Val Val Thr Ser Ala
    1340            1345                1350

Ile Ser Leu Pro Asn Ile Arg Lys Pro Asp Gly Tyr Asp Tyr Tyr
    1355            1360                1365

Ala Phe Ser Lys Asp Gln Tyr Tyr Asn Ile Asp Val Pro Ser Arg
    1370            1375                1380

Thr Ala Arg Ala Ile Thr Thr Arg Ser Gly Gln Thr Leu Ser Lys
    1385            1390                1395

Val Trp Tyr Asn Cys Pro
    1400
```

<210> SEQ ID NO 2
<211> LENGTH: 18

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gatgcagggt accccaaa                                                        18

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagactttgg ataaggtctg cc                                                   22
```